(12) United States Patent
Abdul-Khalek

(10) Patent No.: US 9,448,211 B2
(45) Date of Patent: Sep. 20, 2016

(54) ANALYSIS OF EXHAUST GAS

(71) Applicant: Southwest Research Institute, San Antonio, TX (US)

(72) Inventor: Imad Said Abdul-Khalek, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 0 days.

(21) Appl. No.: 14/096,958

(22) Filed: Dec. 4, 2013

(65) Prior Publication Data

US 2015/0153316 A1 Jun. 4, 2015

(51) Int. Cl.
*G01N 33/00* (2006.01)
*G01N 31/00* (2006.01)

(52) U.S. Cl.
CPC ........ *G01N 31/005* (2013.01); *G01N 33/0014* (2013.01); *G01N 33/0047* (2013.01); *Y10T 436/204998* (2015.01)

(58) Field of Classification Search
CPC .. G01N 31/005; G01N 31/00; G01N 33/182; G01N 33/18; G01N 33/00; Y10T 436/00; Y10T 436/11; Y10T 436/21
USPC ................................. 436/133, 127
See application file for complete search history.

(56) References Cited

U.S. PATENT DOCUMENTS

| 3,762,878 A | * | 10/1973 | Villalobos | G01N 1/405 422/54 |
| 4,042,332 A | * | 8/1977 | Saitoh | C07C 7/14816 436/141 |
| 4,302,422 A | * | 11/1981 | Takahashi | G01N 30/14 422/88 |
| 8,516,908 B2 | | 8/2013 | Wei | |
| 2002/0150522 A1 | * | 10/2002 | Heim | B01D 53/04 423/245.1 |
| 2003/0121481 A1 | * | 7/2003 | Dodd et al. | 123/3 |

OTHER PUBLICATIONS

Paulson S. et al, Total Non-Methane Organic Carbon: Measurements of Total Ad Speicated Hydrocarbons At Azusa, California, Atmospheric Sciences Dept., University of California at Lost Angeles, Los Angeles, CA 90095-1565, date created on line 20 Oct. 1999.*

ICAC (Institute of Clean Air Companies) Proposed Conditional Test Method (CTM-042) "Use of Flame Ionization Detector-Methane Cutter Analysis Systems for VOC Compliance Testing of Bakerie"; Revision submitted by ICAC on Aug. 18, 2004 (11 pgs); <<http://www.epa.gov/ttnemc01/ctm/ctm-042.doc>> (accessed Oct. 17, 2013).

NARSTO Measurements Methods Compendium (39 pgs); << http://cdiac.ornl.gov/programs/NARSTO/Compendium_combined.pdf >> (accessed Oct. 16, 2013).

NETT21 (New Environmental Technology Transfer in the 21st Century): "GEC Environmental Technology Database" (3 pgs) downloaded from http://nett21.gec.jp/gec/database/ Oct. 30, 2013; "Air Pollution continuous Monitoring Technology in Japan" (5 pgs) <<http://www.gec.jp/CTT_DATA/index_amon.html and http://www.gec.jp/CTT_DATA/AMON/CHAP_4/html/Amon-065html>> (accessed Oct. 30, 2013).

S. Paulson, et al; "Total Non-Methane Organic Carbon: Measurements of Total and Speciated Hydrocarbons at Azusa, California", Atmospheric Sciences Dept., Univ of CA at Los Angelos, Los Angelos, CA 90095-1565 USA (9 pgs) <<http://www.cert.ucr.edu/~carter/epacham/paulson.pdf>> (accessed Oct. 2013).

P.W. Perkins Co., Inc.; Removing CO2, How it Works, DECARBITE, Absorbents for the Removal of Carbon . . . How DECARBITE® Works; (2 pgs) <<http://www.pwperkins.com/how_decarbite_works.html>> (accessed Oct. 30, 2013).

SAE International "Development of the direct Nonmethane Hydrocarbon Measurement Vehicle Testing"; Paper # 2003-01-0390 Published Mar. 3, 2003 (2 pgs) <<http://papers.sae.org/2003-01-03901/>> (accessed Oct. 18, 2013).

O. Saenz, Jr. et al; "Measurement of Non-Methane Hydrocarbons", U.S. Dept. of Commerce, National Technical Information Service, Jun. 1971 (36 pgs).

USEPA (United States Environmental Protection Agency); "Determination of total Gaseous Non-Methane Organic Emissions as Carbon"; Method No. SC25.1, Feb. 26, 1991, (74 pgs), << http://yosemite.epa.gov/r9/r9testmethod.nsf/Districts/ECC16339028EA67C88256FC6000A4C4B>> (accessed Dec. 9, 2013).

K. Yamauchi, et al "Absorption and Release of Carbon Dioxide With Various Metal Oxides and Hydroxides"; Materials Transactions, vol. 48, No. 10 (2007) pp. 2739 to 2742.

* cited by examiner

*Primary Examiner* — Christine T Mui
(74) *Attorney, Agent, or Firm* — Grossman, Tucker et al.

(57) ABSTRACT

A method and system of measuring non-methane hydrocarbons in exhaust gas. The method includes sampling exhaust gas, wherein the exhaust gas includes native carbon dioxide, non-methane hydrocarbons and methane. The native carbon dioxide present in the exhaust gas is removed followed by oxidation of the non-methane hydrocarbons to produce carbon dioxide. The concentration of carbon dioxide is then measured and provides a direct indication of the non-methane hydrocarbon concentration.

21 Claims, 4 Drawing Sheets

ANALYSIS OF EXHAUST GAS

FIELD

The present disclosure relates to analysis of exhaust gas from the combustion of hydrocarbon fuel. In particular, the present disclosure measures non-methane hydrocarbon concentration and, in particular, provides a direct measurement of non-methane hydrocarbon concentration contained in hydrocarbon combustion exhaust.

BACKGROUND

When combustion of hydrocarbon fuel in internal combustion engines and furnaces is ideal and complete, the combustion products and exhaust include carbon dioxide and water. However, due to incomplete combustion unburned hydrocarbons, partially burned hydrocarbons, and thermal crack products, as well as nitrogen and sulfur containing byproducts may be present in the exhaust. Some components of exhaust, such as carbon monoxide, hydrocarbons, and nitrogen monoxide (which converts to nitrogen dioxide), are believed to adversely affect the environment as well as humans. Thus, many components of exhaust gas, including non-methane hydrocarbons, are now regulated.

One conventional method of determining non-methane hydrocarbon concentration in engine exhaust or dilute engine exhaust includes the separate measurement of total hydrocarbons and methane in the exhaust. The concentration of non-methane hydrocarbons is then determined from the difference between the total hydrocarbon concentration and methane concentration. However, this method is indirect and a variety of factors influence the measurement of these values. Such factors include engine technology, methods used to measure the total hydrocarbon concentration and methane concentration, and the ratio of total hydrocarbon concentration to methane concentration. These factors can lead to errors and negative non-methane hydrocarbon emission values. This is particularly the case when methane concentration is close in value to total hydrocarbon concentration.

Direct measurements using gas chromatography (GC) have also been used to determine non-methane hydrocarbon concentration in exhaust gas. During GC, the various constituents (i.e., methane, non-methane hydrocarbons, etc.) are separated out of the exhaust gas. However, this process is relatively expensive and time consuming. Furthermore, the method is dependent on a number of factors, such as the flow rate of the analyte through the column and the size and composition of the stationary phase, etc.

Thus room remains for improvement in the measurement of non-methane hydrocarbon concentration present in exhaust gas.

SUMMARY

An aspect of the present disclosure is directed to measuring non-methane hydrocarbons in exhaust gas. The method comprises sampling exhaust gas, wherein the exhaust gas includes native carbon dioxide, non-methane hydrocarbons and methane, removing the native carbon dioxide present in the exhaust gas and oxidizing the non-methane to produce carbon dioxide. One may then measure the concentration of carbon dioxide produced by oxidation of the non-methane hydrocarbons to provide a non-methane hydrocarbon concentration.

Another aspect of the present disclosure is directed to method of measuring non-methane hydrocarbons in exhaust gas including native carbon dioxide, non-methane hydrocarbons and methane. The method includes: (a) supplying exhaust gas to a carbon dioxide remover to remove the native carbon dioxide; (b) supplying the exhaust gas with carbon dioxide removed to a non-methane hydrocarbon oxidizer to oxidize the non-methane hydrocarbons and produce carbon dioxide; and (c) measuring the carbon dioxide produced in step (b) to determine the concentration of carbon dioxide and determining the concentration of non-methane hydrocarbons in the exhaust gas.

Yet a further aspect of the present disclosure is directed to a system for measuring non-methane hydrocarbons in exhaust gas. The system includes a flow path including an inlet and an outlet; a carbon dioxide remover coupled to the flow path between the inlet and the outlet, configured to remove native carbon dioxide from said exhaust gas. A non-methane hydrocarbon oxidizer is coupled to the flow path between the carbon dioxide remover and the outlet configured to oxidize the non-methane hydrocarbons to carbon dioxide. A carbon dioxide analyzer is coupled to the non-methane hydrocarbon oxidizer and is configured to measure carbon dioxide produced by oxidation of the non-methane hydrocarbons.

BRIEF DESCRIPTION OF THE DRAWINGS

The above-mentioned and other features of this disclosure, and the manner of attaining them, may become more apparent and better understood by reference to the following description of embodiments described herein taken in conjunction with the accompanying drawings, wherein.

DETAILED DESCRIPTION

Figure 1:
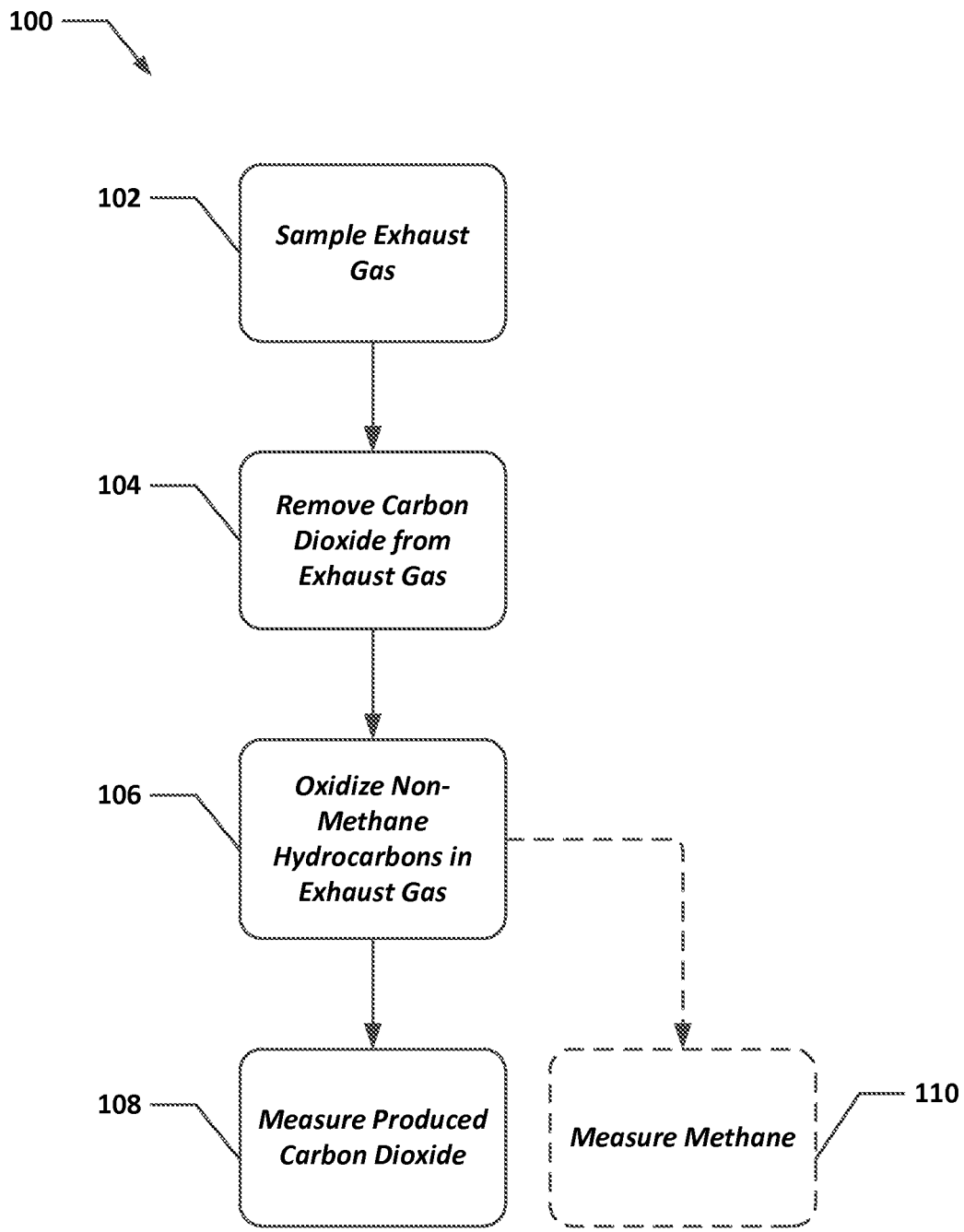
FIG. 1 illustrates a flow chart of an embodiment of a method of measuring non-methane hydrocarbon concentration.

The present disclosure relates to the measurement of non-methane hydrocarbon concentration and, in particular, direct measurement of the concentration of non-methane hydrocarbons emitted in combustion exhaust gas. The combustion of hydrocarbons, which is a primary energy source, results in the production of energy, often in the form of heat. In an internal combustion engine, for example, the heat generated in the process of combusting hydrocarbon fuels causes gases in the combustion chamber (cylinders) to expand. This expansion causes the pistons in the engine to be displaced in the cylinders, rotating a crankshaft and providing motive force. The exhaust is then released from the combustion chamber.

Complete combustion of hydrocarbon fuels results in the production of carbon dioxide and water. However, combustion is often incomplete and components other than hydrocarbons, such as nitrogen and sulfur, may be introduced into the combustion chamber. These factors result in the formation of additional by-products, such as hydrocarbons, carbon monoxide, nitrogen oxides, sulfur oxide and particulate matter.

As noted above, many of the by-products of combustion are regulated and measurements of the various components are made in an attempt to improve the combustion process. One component of interest is non-methane hydrocarbons, which are understood as hydrocarbons other than methane and include, e.g., C2 to C10 alkanes (other than methane), C2 to C10 alkenes, and C2 to C10 alkynes. One method of determining the concentration of non-methane hydrocarbons is to determine the concentration of total hydrocarbons (methane and non-methane hydrocarbons) present in a sample and then determine the concentration of methane in a sample. The difference between the two is then considered to be representative of the non-methane hydrocarbon concentration. However, this indirect measurement (being that the non-methane hydrocarbon concentration is not being measured) proves to be inaccurate in some circumstances.

The present disclosure is directed to methods of measuring concentration of non-methane hydrocarbons in exhaust gas. As may be appreciated from the above, exhaust gas generally includes carbon dioxide, non-methane hydrocarbons, and methane as well as carbon monoxide, nitrogen oxides, sulfur oxides, and other components. Exhaust gas, as understood herein, is produced by the combustion hydrocarbon based fuels, such as but not limited to gasoline, diesel, natural gas, kerosene, and propane. These fuels optionally include additives such as stabilizers, antiknock additives (in the case of gasoline), detergents, ethanol, oxygenate compounds, antistatic agents, corrosion inhibitors, fuel icing inhibitor, and biocides.

In general, the methods include the removal of native carbon dioxide from the exhaust gas, wherein native carbon dioxide is understood as carbon dioxide that is present in the exhaust gas after combustion and prior to sampling and analysis. Then non-methane hydrocarbons are oxidized producing carbon dioxide. The concentration of the carbon dioxide produced by the non-methane hydrocarbons is determined and correlates to the non-methane carbon number concentration. This methodology, therefore, is based on the concentration of the non-methane hydrocarbons, rather than on a measured difference between total hydrocarbon concentration and methane concentration.

An embodiment of measuring non-methane hydrocarbon concentration in exhaust gas is illustrated in FIG. 1. In this embodiment, the method 100 includes sampling exhaust gas 102, removing native carbon dioxide from the exhaust gas 104, oxidizing non-methane hydrocarbons in the exhaust gas 106 to produce carbon dioxide, and measuring the concentration of carbon dioxide produced by the oxidation of the non-methane hydrocarbons 108 to determine the concentration of carbon, indicating the concentration of non-methane hydrocarbons present in the exhaust gas. Optionally, methane concentration is measured at 110 by a flame ionization detector.

Figure 2:
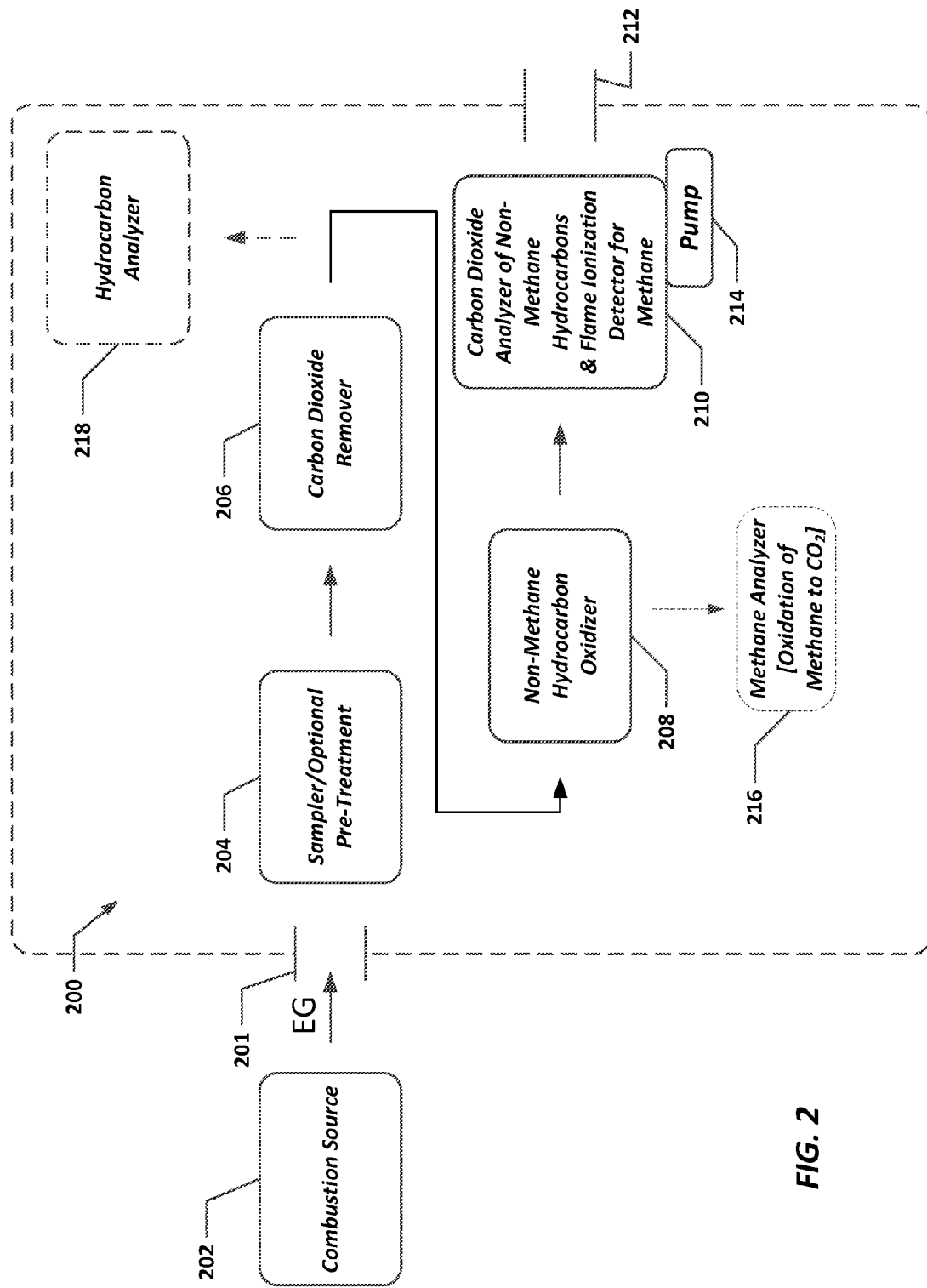
FIG. 2 illustrates a schematic of an embodiment of a system for measurement of non-methane hydrocarbon concentration.

Expanding on the above, reference is now made to the embodiment of a measurement system 200 illustrated in FIG. 2. Exhaust gas EG is sampled from a combustion source 202, such as a combustion engine, including internal combustion engines, or furnaces that utilize hydrocarbon fuels such as propane, natural gas, or heating oil. Sometimes referred to as an "emissions bench", the system includes instrumentation or analytical components, that are now configured to: (1) analyze one or more properties of exhaust gas generated by a combustion source; or (2) modify one or more of the constituents of the exhaust gas, such as removing native carbon dioxide. The exhaust gas flows into inlet 201, through a flow path (represented by arrows) that is coupled to and between the various analytical components, and out the system through an outlet 212.

As illustrated, after entering the inlet 201, the exhaust gas EG flows into sampler 204. The sampler 204 may include a canister, bag, or tube for receiving gas from a combustion source 202. Other components may be associated with or present in the sampler 204 as well, such as one or more pressure monitors, proportional valves for regulating the flow of gas within the system in conjunction with vacuum pumps, or other devices for regulating and modulating the flow of the exhaust gas.

The sampled exhaust gas is either used raw or is preconditioned. Raw gas is understood as sample gas that is supplied to testing equipment in an undiluted and otherwise relatively untreated state. In those embodiments where the sampled exhaust gas is treated, the gas is diluted. In addition, or alternatively, factors such as temperature, concentration of species in the gas, presence of particulate matter, the amount of condensation, and the presence of volatiles are adjusted. For example, the temperature of the exhaust gas may be cooled to room temperature before measurement. However, as cooling may lead to supersaturation of various by-products, such as water, sulfur compounds, and hydrocarbons, the gas is preferably diluted by an inert gas to avoid supersaturation. An inert gas is understood as a gas that does not react with the compounds of interest present in the exhaust gas.

Native carbon dioxide is then removed from the exhaust by passing the exhaust gas (EG) into a carbon dioxide remover 206. The carbon dioxide remover preferably operates through either absorption or adsorption utilizing a carbon dioxide removal media including metal oxides, such as lithium oxide and calcium oxide; hydroxides, such as sodium or calcium hydroxide; or lithium silicates, such as ortholithium silicate, to absorb or adsorb the carbon dioxide.

The operating temperature for carbon dioxide removal preferably ranges from −100° C. to 700° C., including all values and ranges therein, and depend, in part, on the selected removal media. For example, removal of carbon dioxide with sodium hydroxide can be performed in the range of 20° C. to 35° C. and removal of carbon dioxide with lithium silicate can be performed at 500° C. to 700° C. Operating temperatures of 191° C. or higher, such as up to 700° C., are particularly preferred to be consistent with current 40 CFR Part 1065 regulations as these temperatures are used as sample line temperatures of the hydrocarbon analyzer to avoid hydrocarbon losses in the sample lines.

In addition, depending on the removal media, removal is reversible and the carbon dioxide may be released by the removal media. For example, lithium silicate releases absorbed carbon dioxide at temperatures of 700° C. to 1,000° C., including all values and ranges therein. Other removal media that release captured carbon dioxide include, for example, calcium oxide and calcium hydroxide. Sodium hydroxide $CO_2$ absorption, by contrast, is irreversible.

As may be appreciated, different removal media exhibit different carbon dioxide removal efficiency. The efficiency of carbon dioxide removal herein by the removal media is preferably in the range of 99.0% to 99.99999%, including all values and ranges therein, such as 99.999% to 99.99999%. However, a relatively small fraction of native carbon dioxide may slip through the selected carbon dioxide remover, wherein the native carbon dioxide slip is in the range of 0.001% to 0.00001% of the total native carbon dioxide that enters the carbon dioxide remover.

In particular embodiments, the carbon dioxide remover may employ sodium hydroxide granules, such as DECARBITE available from P.W. Perkins Co. Inc., as a removal media. The carbon dioxide contacts moisture present with the sodium hydroxide granules to form carbonic acid. The carbonic acid then reacts with sodium hydroxide to form sodium carbonate and water. The removal of the carbon dioxide occurs at a temperature in the range of 20° C. to 35° C. and a removal rate in the range of 99.99999% efficiency can be achieved.

After removal of the carbon dioxide, the exhaust gas is passed through a non-methane hydrocarbon oxidizer 208 to oxidize the non-methane hydrocarbons producing carbon dioxide. The non-methane hydrocarbon oxidizer utilizes a heated non-methane hydrocarbon catalyst to oxidize the non-methane hydrocarbons. The oxidation catalyst preferably includes, for example, platinum or palladium supported on a cordierite or metallic foil honeycomb by a washcoat of alumina or silica. The oxidation catalyst is preferably heated to a temperature that is less than the decomposition temperature of methane. The oxidation catalyst is preferably heated at a temperature in the range of 200° C. to 400° C., including all values and ranges therein. At such temperatures, as explained herein, there is nearly complete conversion of non-methane hydrocarbons to $CO_2$ with little or no conversion of methane to $CO_2$.

As methane oxidizes at relatively higher temperatures, and the catalyst is heated to a temperature below the decomposition temperature of methane, less than or equal to 15% of the total methane content of the exhaust gas converts to carbon dioxide, such as in the range of 0% to 15%, 1% to 10%, 1% to 5%, 1% to 3%, etc. This is expressed herein as the methane conversion efficiency. In addition, the oxidation catalyst is preferably at least 85% efficient in oxidizing the total amount of non-methane hydrocarbons present in the exhaust gas, and preferably is in the range of 90% to 99.9% efficient, including all values and ranges therein, and more preferably in the range of 98% to 100% efficient.

The exhaust gas, now including the carbon dioxide produced by oxidizing non-methane hydrocarbons, then passes to a carbon dioxide analyzer 210 to measure the concentration of carbon dioxide. The carbon dioxide analyzer preferably includes a nondispersive infrared detector (NDIR). In a nondispersive infrared detector, infrared light is directed through a sample chamber as well as a parallel reference chamber including reference gas. A detector measures the amount of light absorbed at given frequencies by the gas. Based on the amount of light absorbed, the detector is able to measure a volumetric concentration of carbon monoxide or carbon dioxide in the sample. A light filter and optionally a light modulator are provided between the sample and the detector, which filters out light outside of the spectrum of interest. The measured carbon dioxide concentration provides a direct measurement of non-methane carbon number concentration in the analyzed exhaust gas.

The residual methane concentration (i.e. the methane not subject to oxidation in the non-methane hydrocarbon oxidizer) may also be measured, and there are two options. The concentration of methane may be determined by the carbon dioxide analyzer 210 provided it is configured to measure methane. For example, the carbon dioxide analyzer may include a flame ionization detector for measurement of the residual methane concentration. Upon entering the flame ionization detector, which is kept at elevated temperatures to prevent condensation, the gas is mixed with hydrogen fuel and an oxidant. A positive bias voltage is applied to repel reduced carbon ions towards collector plates, which act as an ammeter and detect the carbon ions hitting the plates. This then creates a signal, which may be amplified, and is representative of the concentration of methane present in the sample.

One may also include a methane analyzer 216. A sample of the exhaust gas may be diverted before or after the carbon dioxide analyzer 210 to the methane analyzer 216. The methane analyzer 216 includes a heated methane catalyst and a carbon dioxide analyzer, such as a non-dispersive infrared detector. In such embodiments, the heated methane catalyst converts the methane into carbon dioxide. The methane catalyst may be selected from the non-methane hydrocarbon catalysts described above, except operated at relatively higher temperatures so that it now oxidizes the methane to $CO_2$. For example, it may be operated at temperatures greater than 400° C., and in the range of up to 600° C. At 216, the concentration of the carbon dioxide produced by the oxidized methane is then measured with the carbon dioxide analyzer to provide an indication of the methane concentration.

In addition, prior to oxidation of the non-methane hydrocarbons, the concentration of the total hydrocarbons present in the exhaust gas may be determined for comparative purposes using a hydrocarbon analyzer 218. While the hydrocarbon analyzer 218 is depicted as being coupled to the flow path between the carbon dioxide remover 206 and carbon dioxide remover 208, it may be coupled prior to the carbon dioxide remover 206 as well. In embodiments, the hydrocarbon analyzer includes a flame ionization detector, which functions similarly to that described above. However, the signal is representative of the concentration of the total hydrocarbons present in the sample, rather than just the methane.

The flow rate of the exhaust gas through the measurement system is preferably driven by a pump 214 associated with the system 200 and connected to the flow path between the inlet 201 and outlet 212. An internal pump 214 of the carbon dioxide analyzer 210, discussed further herein, is sufficient to draw the exhaust gas from the inlet 201 of the measurement system 200 to the outlet 212 of the measurement system 200. In other embodiments, a pump is connected between the carbon dioxide analyzer and the outlet. The pump provides an exhaust gas flow in the range of 0.5 standard liter per minute (slpm) to 3.0 slpm, including all values and ranges therein.

The flow path, from the inlet 210 to the outlet 212, including between the various components such as the sampler 204, carbon dioxide remover 206, non-methane hydrocarbon oxidizer 208, carbon dioxide analyzer 210, optional methane analyzer 216 and optional total hydrocarbon analyzer 218, is preferably heated at a temperature above the dew point of the exhaust gas, such as in the range of 25° C. to 60° C., including all values and ranges therein. In using raw gas, the system may be heated to a temperature in the range of 35° C. to 60° C., including all values and ranges therein. It may be appreciate that in operating the system at temperatures in this range no preconditioning is needed. In using diluted gas, the system may be heated to a temperature in the range of 25° C. to 35° C., including all values and ranges therein. Further, as noted above, each analytical component (i.e., sampler, carbon dioxide remover, non-methane hydrocarbon oxidizer, carbon dioxide analyzer, etc.) may operate at a different temperature depending on the requirements of the function provided by the component.

As can be appreciated, the efficiency of native carbon dioxide removal from the exhaust gas and efficiency of non-methane hydrocarbon to carbon dioxide conversion may be less than 100%. In addition, during oxidation of non-methane hydrocarbons, a portion of methane may be converted to carbon dioxide. These conditions may generate artifacts in the measurement and detract from the accuracy of the measurement of the carbon dioxide concentration that is produced by the non-methane hydrocarbons. Accordingly, the present disclosure is also directed to taking into account these artifacts and correcting the non-methane carbon number concentration measured by the system.

Figure 3:
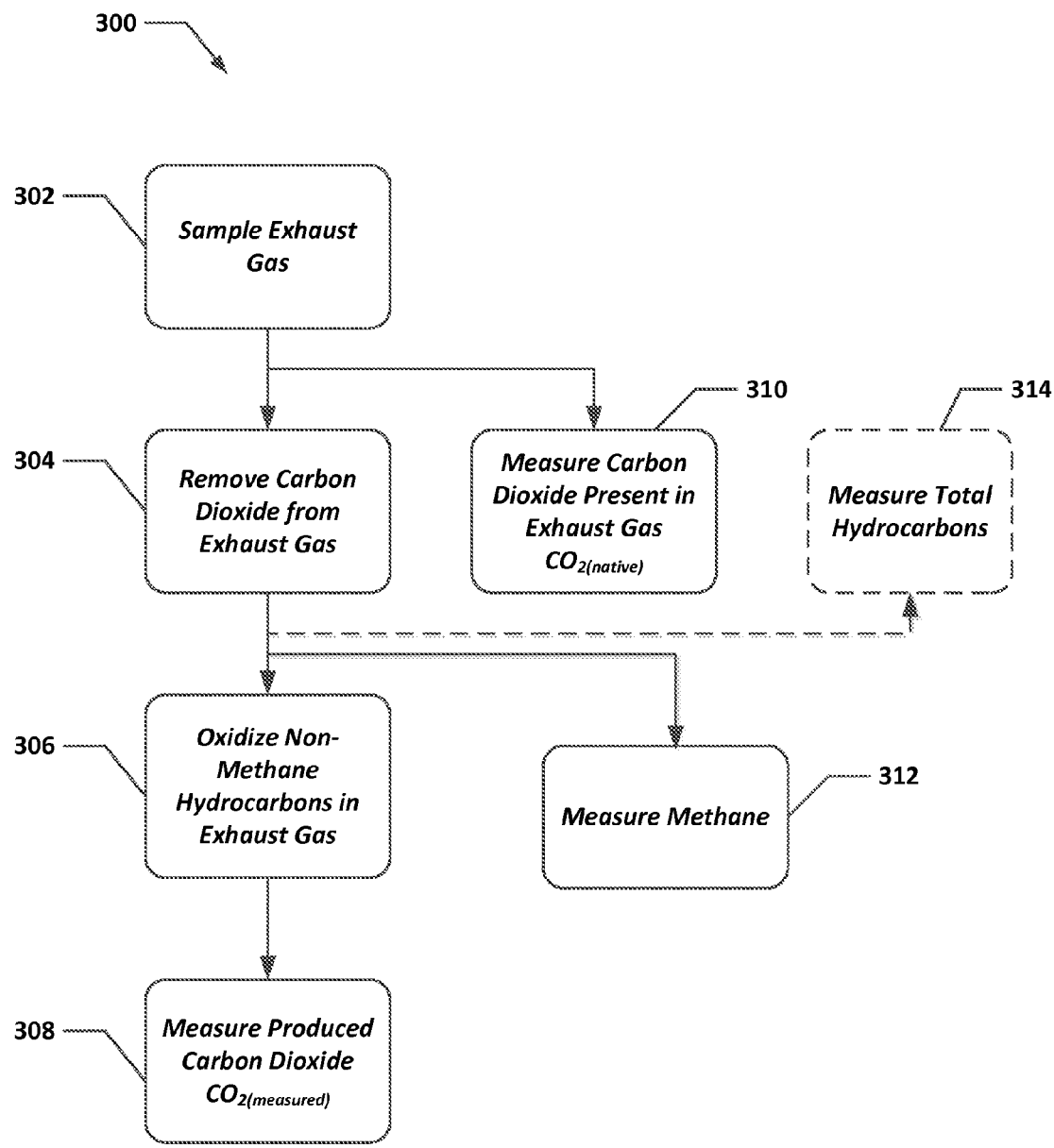
FIG. 3 illustrates a flow chart of an embodiment of a method of correcting non-methane hydrocarbon concentration measurements.

FIG. 3 illustrates an embodiment of calculating and correcting the non-methane carbon number concentration by taking into consideration: (1) the carbon dioxide remover efficiency; (2) the oxidation of residual methane during oxidation of the non-methane hydrocarbons; and (3) the non-methane hydrocarbon oxidizer oxidation efficiency.

Carbon Dioxide Remover Efficiency

As illustrated, the concentration of native carbon dioxide $CO_{2(native)}$ in the exhaust gas is measured 310 prior to removing the carbon dioxide from the gas at 304. In one embodiment, the concentration of native carbon dioxide that slips through the carbon dioxide remover without actually being removed is then calculated based on the known efficiency of the carbon dioxide remover. For example, the measured quantity of native carbon dioxide $CO_{2(native)}$ entering the system is multiplied by an efficiency factor $E_f$ of the carbon dioxide remover, wherein the efficiency factor $E_f$ is difference between 100% and the % efficiency of the carbon dioxide remover (which is, as described above, in the range of 99.0% to 99.99999%). In addition, or alternatively, the concentration of native carbon dioxide $CO_{2(native)}$ that passes through the carbon dioxide remover is directly measured from the exhaust gas prior to the oxidation of the non-methane hydrocarbons at 306. In either of the above embodiments the measurements may be performed by non-dispersive infrared detection techniques. These methods provide an indication of artifacts generated due to native carbon dioxide $CO_{2(native)}$ slipping through the carbon dioxide remover, which artificially increases the determined amount of non-methane carbon content at 308. Thus, the concentration of native carbon dioxide slip determined by either of these measurements is subtracted from the non-methane carbon concentration measured by the carbon dioxide analyzer in step 308.

Oxidation of Methane During Oxidation of the Non-Methane Hydrocarbons

With reference again to FIG. 3, the concentration of methane $CH_{4(conc.)}$ that is introduced into the non-methane hydrocarbon oxidizer 306 is measured 312. Based on the concentration of methane $CH_{4(conc.)}$ measured, the concentration of methane that is oxidized $CH_{4(ox)}$ by the non-methane hydrocarbon oxidizer is calculated from the established methane conversion efficiency rates $E_{mc}$ of the hydrocarbon oxidizer 306, which is (as described above) 15% or less. Specifically, the concentration of oxidized methane $CH_{4(ox)}$ is calculated by multiplying the methane conversion efficiency rate $E_{mc}$ with the measured concentration of methane $CH_{4(conc.)}$. This number then provides an indication of artifacts in the non-methane carbon concentration due to any oxidation of methane into $CO_2$ at step 306.

For example, the total hydrocarbon concentration in the exhaust gas may be 10 ppm, and formed from 5 ppm of methane and 5 ppm of non-methane hydrocarbons. The methane conversion efficiency is determined to be 5%. The $CO_2$ artifacts from the methane is then calculated to be equal to (0.05)*5 ppm=0.25 ppm. From this calculation, the non-methane measurement by the $CO_2$ analyzer at 308 will be 5.25 ppm and 0.25 ppm will be subtracted as that amount due to oxidation of methane.

In other embodiments, the concentration of methane is measured after passage of the exhaust gas through the oxidizer 306. The concentration of methane introduced into the non-methane hydrocarbon oxidizer 306 as well as the concentration of methane that is oxidized by the non-methane hydrocarbon oxidizer 306 may be determined based on the established methane conversion efficiency rates $E_{mc}$, of the hydrocarbon oxidizer 306.

For example, the measured methane concentration after passing through the non-methane oxidizer may be determined to be 4.75 ppm. The total methane concentration may then be calculated by dividing this number by the difference between 100% and the methane conversion efficiency, which is determined to be 5%, or 95%. This then indicates that 5 ppm of methane was originally present in the exhaust gas prior to passing the exhaust gas through the non-methane hydrocarbon oxidizer. The $CO_2$ artifacts from the methane is then calculated to be equal to (0.05)*5 ppm=0.25 ppm. From this calculation, the non-methane measurement by the $CO_2$ analyzer at 308 will be 5.25 ppm and 0.25 ppm will be subtracted as that amount due to oxidation of methane.

Non-Methane Hydrocarbon Oxidizer Oxidation Efficiency

The concentration of non-methane hydrocarbons (NMHC) that are not converted to carbon dioxide by the non-methane hydrocarbon oxidizer and slip through the oxidizer may also be considered. To determine such NMHC slip, the measured carbon dioxide concentration $CO_{2(measured)}$ is adjusted by a known efficiency factor of the non-methane hydrocarbon oxidizer for converting non-methane hydrocarbons into carbon dioxide $E_{con}$. The efficiency factor $E_{con}$ is the difference between 100% and the % efficiency of the non-methane hydrocarbon oxidizer for oxidizing the non-methane hydrocarbons (which is, as described above, at least 85%). Accordingly, once the efficiency factor is known, and one measures the produced $CO_2$ at step 308, one may upwardly adjust the amount of non-methane hydrocarbons determined from such measured quantity of $CO_2$, by the considered amount of NMHC slip.

For comparative purposes, the concentration of total hydrocarbons in the sample is optionally determined prior to oxidation 314 as illustrated in FIG. 3. Alternatively, although not illustrated, the concentration of total hydrocarbons in the sample may be measured prior to removing the carbon dioxide from the exhaust gas. However, in embodiments of the above, a determination of the total hydrocarbon concentration is not necessary and is not necessarily performed.

Figure 4:
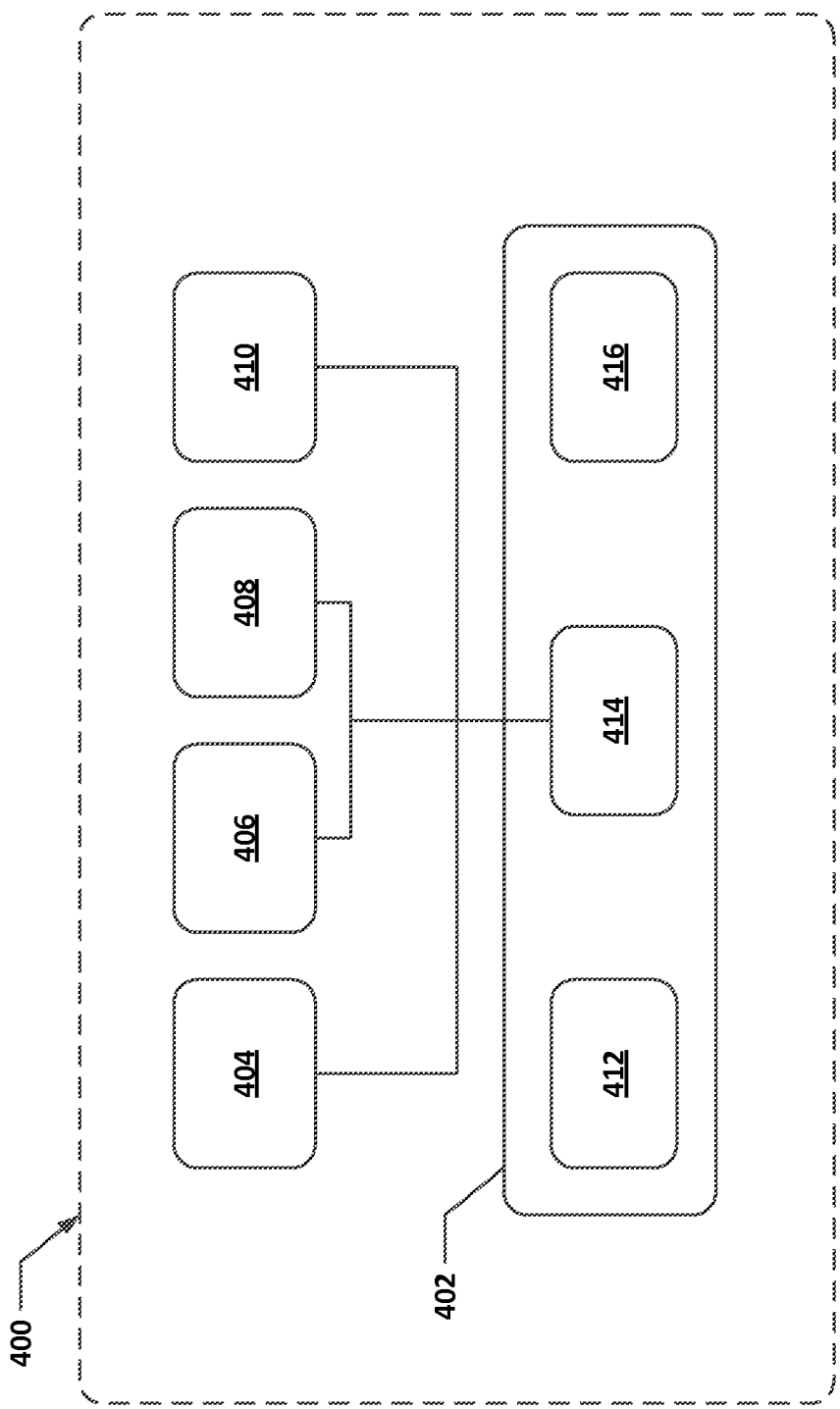
FIG. 4 illustrates a schematic of an embodiment of circuitry for quantifying non-methane hydrocarbon concentration.

In a related embodiment, and as illustrated in FIG. 4, one may provide a system 400 including circuitry for controlling the individual components and calculating the non-methane carbon concentration. As illustrated in FIG. 4, the circuitry 402 is operatively coupled to one or more analytical components in the system 400 (such as sampler 404, carbon dioxide remover 406, non-methane hydrocarbon oxidizer 408, and carbon dioxide analyzer 410) and is used to quantify voltages to provide measurements of the compounds in the exhaust gas and to correct measurement errors. Operatively coupling is understood herein as providing an electrical connection (including a wireless connection), mechanical connection, or both. As illustrated in FIG. 4, the circuitry 400 includes, in embodiments, a processor 412, interfaces 414 for interfacing with analytical components 404, 406, 408, 410 in the system, as well as one or more user interfaces 416.

Analytical component interfaces may include wiring or wireless devices coupling the processor to the analytical components. The user interface 416 may include a display, a mouse, a keyboard or other devices. Communication between the components of the control circuitry may be through electrical wires or performed wirelessly.

Any of the operations described herein may be implemented in a system that includes one or more tangible storage mediums having stored thereon, individually or in combination, instructions that when executed by one or more processors perform the methods. Here, the processor may include, for example, a system CPU and/or other programmable circuitry. Also, it is intended that operations described herein may be distributed across a plurality of physical devices, such as processing structures at more than one different physical locations including within the various analytical components 404,406,408,410. The storage medium may include any type of tangible medium, for example, any type of disk including floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of media suitable for storing electronic instructions. Other embodiments may be implemented as software modules executed by a programmable control device.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

What is claimed is:

1. A method of measuring non-methane hydrocarbons in exhaust gas, comprising:
   sampling exhaust gas, wherein said exhaust gas includes native carbon dioxide, non-methane hydrocarbons and methane;
   removing said native carbon dioxide present in said exhaust gas at a temperature in the range of −100° C. to 700° C. to provide a mixture of non-methane hydrocarbons and methane;
   oxidizing said non-methane hydrocarbons present in said mixture of said non-methane hydrocarbons and said methane at a temperature in the range of 200° C. to 400° C. to produce carbon dioxide and provide a mixture of said carbon dioxide and said methane; and
   measuring a concentration of said carbon dioxide in said mixture of said carbon dioxide and said methane to provide a non-methane hydrocarbon concentration.

2. The method of claim 1, wherein removing said native carbon dioxide present in said exhaust gas comprises using carbon dioxide removal media.

3. The method of claim 2, wherein said carbon dioxide removal media includes sodium hydroxide.

4. The method of claim 1, wherein oxidizing said non-methane hydrocarbons comprises passing said exhaust gas through a non-methane hydrocarbon oxidizer including a heated non-methane hydrocarbon oxidation catalyst.

5. The method of claim 4, further comprising adjusting said measured concentration of said carbon dioxide based on the efficiency of said non-methane hydrocarbon oxidizer to oxidize methane.

6. The method of claim 5 wherein said efficiency of said non-methane hydrocarbon oxidizer to oxidize methane comprises oxidizing up to 15% of said methane in said exhaust gas.

7. The method of claim 1, further comprising adjusting said measured concentration of said carbon dioxide based on the efficiency of said non-methane hydrocarbon oxidizer to oxidize non-methane hydrocarbons.

8. The method of claim 7 wherein said efficiency of said non-methane hydrocarbon oxidizer to oxidize non-methane hydrocarbons comprises oxidizing 85% or more of said non-methane hydrocarbons.

9. The method of claim 1, wherein measuring said carbon dioxide in said mixture of said carbon dioxide and said methane uses non-dispersive infrared analysis.

10. The method of claim 1, wherein said exhaust gas is sampled from an internal combustion engine.

11. The method of claim 1, further comprising adjusting said measured concentration of said carbon dioxide based on the efficiency of native carbon dioxide removal from said exhaust gas.

12. The method of claim 11 wherein said efficiency of native carbon dioxide removal from said exhaust gas comprises removing 99.0% or more of said native carbon dioxide.

13. A method of measuring non-methane hydrocarbons in exhaust gas including native carbon dioxide, non-methane hydrocarbons and methane, comprising:
   (a) supplying exhaust gas to a carbon dioxide remover to remove said native carbon dioxide, wherein said carbon dioxide remover is operated at a temperature in the range of −100° C. to 700° C. to provide a mixture of non-methane hydrocarbons and methane;
   (b) supplying said mixture of said non-methane hydrocarbons and said methane to a non-methane hydrocarbon oxidizer to oxidize said non-methane hydrocarbons at a temperature in the range of 200° C. to 400° C. to produce carbon dioxide and provide a mixture of said carbon dioxide and said methane; and
   (c) measuring the carbon dioxide produced in step (b) in said mixture of said carbon dioxide and said methane to determine the concentration of said carbon dioxide and determining the concentration of non-methane hydrocarbons in said exhaust gas.

14. The method of claim 13 further comprising adjusting said measured concentration of said carbon dioxide in step (c) based upon the efficiency of said non-methane hydrocarbon oxidizer to oxidize methane.

15. The method of claim 13 further comprising adjusting said measured concentration of carbon dioxide in step (c) based on the efficiency of said non-methane hydrocarbon oxidizer to oxidize non-methane hydrocarbons.

16. The method of claim 13 further comprising adjusting said measured concentration of said carbon dioxide in step (c) based on the efficiency of native carbon dioxide removal from said exhaust gas.

17. A system for measuring exhaust gas containing non-methane hydrocarbons, methane and native carbon dioxide, comprising:
   a flow path including an inlet and an outlet;
   a carbon dioxide remover coupled to said flow path between said inlet and said outlet, configured to remove native carbon dioxide from said exhaust gas at a temperature in the range of −100° C. to 700° C. to provide a mixture of non-methane hydrocarbons and methane;

a non-methane hydrocarbon oxidizer coupled to said flow path between said carbon dioxide remover and said outlet configured to oxidize said non-methane hydrocarbons to carbon dioxide at a temperature in the range of 200° C. to 400° C. and provide a mixture of said carbon dioxide and said methane; and a carbon dioxide analyzer coupled to said non-methane hydrocarbon oxidizer configured to measure carbon dioxide produced by oxidation of said non-methane hydrocarbons in said mixture of said carbon dioxide and methane.

18. The system of claim 17 wherein said system adjusts said measured concentration of said carbon dioxide based upon the efficiency of said non-methane hydrocarbon oxidizer to oxidize methane.

19. The system of claim 17 wherein said system adjusts said measured concentration of said carbon dioxide based on the efficiency of said non-methane hydrocarbon oxidizer to oxidize said non-methane hydrocarbons.

20. The system of claim 17 wherein said system adjusts said measured concentration of said carbon dioxide based on the efficiency of said carbon dioxide remover to remove native carbon dioxide from said exhaust gas.

21. The method of claim 1, removing said native carbon dioxide present in said exhaust gas at a temperature in the range of 191° C. to 700° C.

* * * * *